United States Patent [19]

Repine

[11] Patent Number: 4,650,897

[45] Date of Patent: Mar. 17, 1987

[54] ORGANIC SYNTHESIS

[75] Inventor: Joseph T. Repine, Ann Arbor, Mich.

[73] Assignee: Warner-Lambert Co., Morris Plains, N.J.

[21] Appl. No.: 735,933

[22] Filed: May 20, 1985

[51] Int. Cl.[4] .................................. C07C 125/065
[52] U.S. Cl. ............................................. 560/160
[58] Field of Search ..................... 560/160; 562/401

[56] References Cited

U.S. PATENT DOCUMENTS 4,397,786  8/1983  Evans .................................. 260/404
4,487,963  12/1984  Bock .................................. 560/160

Primary Examiner—Michael L. Shippen
Attorney, Agent, or Firm—Sandra M. Person

[57] ABSTRACT

The natural 3S, 4S isomer of the protected amino acid Boc-statine can be efficiently produced in large quantities using a novel method.

1 Claim, No Drawings

ORGANIC SYNTHESIS

BACKGROUND

Statine (4S-amino, 3S-hydroxy, 6-methylheptanoic acid) is of pharmaceutical interest as a key intermediate in the preparation of inhibitors of proteases such as pepsin and renin. It is disclosed as compound No. 8652 at page 1258 of *The Merck Index*, 10th edition (1983). Its structure is:

$(CH_3)_2CHCH_2CH(NH_2)CH(OH)CH_2CO_2H.$

It has been demonstrated that pepsin inhibitors containing the unnatural 3R, 4S isomer of statine exhibit as much as a thousand-fold decrease in activity when compared to their counterparts prepared from the naturally occuring 3S, 4S isomer. See Liu, W.; Smith, S.; Glover, G.; *J. Med. Chem.* Vol. 22, No. 5 577–579 (1979, CA 90:161943h); Kawai, M.; Boparai, A.; Bermatowicz, M.; Rich, D.; *J. Org. Chem.*, 48, No. 11, 1876–1879 (1983, CA 98; 215995Z); and Rich, D. H.; Son, Eric, T. O.; *J. Med. Chem.* 23, No. 1, 27–33 (1980, CA 52413F). For these reasons it has become desirable to prepare Boc-3S, 4S statine in large quantities for synthetic purposes. Its structure is:

$(CH_3)_2CHCH_2CH(NHR)CH(OH)CH_2CO_2H$ wherein R is $C(O)OC(CH_3)_3$.

Initially, 3S, 4S statine was obtained by the purification of the hydrolysates of a number of pepstatins of pyridomycin, which yielded the natural isomer. However, the scale of these preparative procedures has been increased to only a modest level.

Chiral and diastereomeric statines can be made by a variety of techniques. The chiral methods suffer from various disadvantages. Often, they are multi-step procedures having moderate to poor yields, requiring exotic reagents, which in most cases do not yield a sufficiently high enantiomeric excess or purity to avoid a purification step to remove the unwanted isomer or other contaminants. The diastereomeric procedures, while being synthetically efficient, share with the chiral procedures the necessity for a purification step to remove the unwanted isomer.

Previously, such purification was accomplished by chromatographic methods which are not trivial, in that the Rf values of protected statine isomers are very similar. The selection of various derivatives of, or protecting groups, for the desired product(s) can increase or decrease the difficulty of this separation. See U.S. Pat. No. 4,397,786; Rich, D.; Son, E.; Bopari, A.; J. Org. Chem., Vol. 43, No. 18, 3624–3626 (1978. CA 89: 147704r); Rague, B.; Fehrentz, J.; Guegan, R.; Chapleur, Y., Castro, B.; Bull. Soc. Chem. Fr., 107–8 Pt. 11 230-2 (1983, CA 100; 210370e); and Gesellchen, P.; Univ. of Wisconsin, Madison, Wis., Diss. Abstr. Int. B 38(8) 3703–4, (1978, CA 88; 152951a).

The separation of isomers of Boc-statine by fractional crystallization has only been cited twice in prior literature. In one reference, the separation of 3S, 4S Boc statine from the 3RS, 4S Boc statine mixture was set out. However, it was later determined by another investigator that the product was still a mixture of isomers. That investigator obtained the pure isomers by chromatography. See the Rich et. al. article (cited above) and Steulmann, R.; Klostermeyer, H.; Liebigs Ann. Chem., 2245–2250 (1975, CA 84: 106020f.)

THE INVENTION

The invention deals with a novel method for separating a mixture of 3S and 3R Boc-statine. It is based on the discovery of an amine which can be used to form the salts of a mixture of 3S and 3R Boc-statine, which salts can be separated by fractional crystallization to yield the desired 3S, 4S isomer.

In a preferred embodiment, four crystallizations or less are needed to separate a 55/45 mixture of 3RS, 4S-Boc statine (as the R-(+)-alpha-phenethylamine salt to a purity of 97% in the desired 3S isomer. The isomer can be further purified by regeneration to free the Boc statine acid, which can be crystallized to 100% purity based on HPLC analysis. Overall yield is approximately 70% of the available 3S isomer.

Alpha-phenethylamine, also known as methyl benzylamine conforms to the formula:

$C_6H_5CH(CH_3)NH_2.$

Advantages

The method of this invention has several advantages over known processes for separating this amino acid. The advantages of this procedure over the use of chromatography to make the separation are in the savings of labor, solvent, and column packing. The R-(+)-alpha-phenethylamine can be recovered and reused. Yield may be increased above the claimed 70% by recovery and recycle of the filtrates of the crystallizations, which contain enriched amounts of the correct 3S, 4S isomer in the final two crystallizations.

Other aspects and advantages will be apparent upon consideration of the following description of the invention.

DESCRIPTION OF THE INVENTION

The invention deals with a process for separation of 3S, 4S Boc-statine from the unwanted 3R, 4S Boc-statine formed when the process of U.S. Pat. No. 4,397,786 is carried out.

Typical Procedure

A typical scheme for the production of the R-(+)-alpha-phenethylamine salt of 3S, 4S Boc-statine and the subsequent regeneration of 3S, 4S Boc-statine is described below.

A. Preparation of 3RS, 4S Boc-statine t-Boc leucinaldehyde was prepared from the O,N-dimethyl amide in a similar manner to that described by Rague, B.; et. al.

Crude 3RS, 4S Boc-statine ethyl ester is prepared from this aldehyde and was hydrolysed to 3R,S,4S-Boc-statine as described in U.S. Pat. No. 4,397,786. These procedures are described as follows:

Boc-Leucine-O,N-dimethylamide

A solution was prepared from the addition of Boc-Leucine $H_2O$ (Bachem, 200 g, 0.8 moles) to two liters of 80/20 $MeCl_2$/THF. The solution was dried over $MgSO_4$, filtered, and added to a 5L flask equipped with argon purge and mechanical stirring. The solution was cooled to −18° C. and carbonyldiimadazole (Aldrich, 136.7 g, 0.842 moles) was added, with offgassing. The mixture was stirred for one hour at −15° C. and O,N-dimethylhydroxylamine hydrochloride (Aldrich, 87.4 g, 0.896 moles) was charged, followed by the addition of N-methylpiperidine (Aldrich, 83.96 g, 0.864 moles, 103 ml). Exotherm to −10° C. was observed. The mixture was stirred, and allowed to warm to room temperature overnight. The mixture was stripped to an oil, taken up into 1.5 L ethyl acetate and extracted three times with 1 L of 1N citric acid, once with saturated NaHCO$_3$ solution (500 ml) and once with saturated NaCl solution (300 ml). The organic phase was dried over MgSO$_4$, filtered, and stripped to an oil, 193.2 g, 88% yield.

Theory: C, 56.91; H, 9.55; N, 10.21 Found: C, 56.68; H, 9.22; N, 9.82 Rotation $[\alpha]_D^{23} = -24.7°$ (C=1.54% in methanol)

Boc Leucinal

Boc Leucine-O,N-dimethylamide (180.9 g, 0.66 moles) and 800 ml dry THF were charged to a 5 L flask giving solution. The mixture was cooled to −20° C. Over 15 minutes, a suspension of LiAlH$_4$ (Ventron, 26.24 g, 0.69 moles, 5% excess) in 500 ml THF was charged from a cooled addition funnel, giving vigorous offgassing. The mixture was stirred and allowed to warm to 5° C. over 15 minutes. 3N HCl, approximately 1.2 liters at 0° C. was added as rapidly as possible in small increments, with vigorous offgassing. A paste formed, which later thinned out as pH was adjusted to 3.0. 1L ethyl ether was added and the phases were separated. The aqueous phase was extracted twice with 1 L ethyl ether, and the organic phases were combined. The organic phases were washed with 1 L saturated NaHCO$_3$ solution, 1 L saturated NaCl solution, and dried over MgSO$_4$. The mixture was filtered and stripped of solvent at 30° C. in vacuo, giving an oil, 150.0 g, 105% yield.

Rotation $[\alpha]_D^{23} = -34.2°$ C=1.11 in methanol; $[\alpha]_D^{23} = +15.2°$ C=1.12 in CHCl$_3$.

Material should be stored at −30° C. and used as soon as possible to avoid racemization.

3RS, 4S Boc-Statine Ethyl Ester

To a 3 L flask containing THF (350 ml) was charged diisopropylamine (145.2 ml, 112.09 g, 1.11 moles). The mixture was cooled to −35° C. and N-butyllithium, (2.4M in hexane, 462 ml, 1.11 moles) was charged over 15 minutes. The mixture was cooled to −85° C. over 15 minutes, after which ethyl acetate (108 ml, 97.6 g, 1.11 moles) was added over ten minutes, with temperature not exceeding −80° C. After stirring for 15 minutes at −85° C., the mixture was cooled to −90° C. A solution of boc Leucinaldehyde (159 g, 0.738 moles) in 400 ml THF was cooled to −70° C. and charged from a cooled addition funnel to the mixture over 15 minutes, with temperature not exceeding −80° C. The mixture was stirred at −90° C. for 15 minutes. With rapid stirring, approximately 600 ml of 3N HCl was added, allowing the temperature to rise to −5° C. over the course of the addition, with the pH reaching 2.0 by litmus. The mixture was then warmed to +10° C., and 2 liters of ethyl ether were charged to the mixture with vigorous agitation. The phases were separated, and the aqueous phase was again washed with 1 L ethyl ether. The organic phases were combined, washed with saturated NaHCO$_3$ (400 ml) and saturated NaCl solution, dried over MgSO$_4$, filtered and stripped to an oil, 211.1 g, 94% yield.

Boc-Statine Ethyl Ester Hydrolysis

Boc-Statine Ethyl Ester (222.9 g, 0.755 moles) was charged to a 5 L flask containing 1 L dioxane, giving solution. 1 L H$_2$O was added, giving a cloudy suspension.

A pH meter was standardized at pH 10 using 50/50 dioxane/pH 10 buffer. The meter was used to monitor the addition of 50% NaOH to the mixture over 45 minutes, at a rate that maintained pH at 12.0. After pH had stabilized at 12.0, the mixture was stirred an additional 45 minutes at 25° C. pH was then adjusted to 6.5 with 12% HCl and the dioxane was removed in vacuo, reducing the total volume by approximately one half. The mixture was extracted three times with 1000 ml ethyl acetate to remove impurities. The aqueous phase was cooled to 3° C. and acidified to pH 2 with 12% HCl. This was extracted twice with 1.5 L ethyl acetate, which was washed with 100 ml saturated NaCl solution, dried over MgSO$_4$, filtered and stripped to a solid, 160.8 g, 77% yield.

| HPLC 15453 X5C | | |
| --- | --- | --- |
| Retention Time (min) | Identity | % |
| 1.84 to 3.98 | Unknowns | 7.43 |
| 10.94 | 3R isomer | 38.75 |
| 12.18 | 3S isomer | 48.62 |
| 21.15 | Unknown | 5.19 |

B. Crystallization

1st Crystallization

3RS, 4S Boc-statine (173.38 g, 0.63 mol.) prepared as described above, was dissolved in 11.67 L hot ethyl acetate to which was added 170 ml methanol. To this was added R-(+)-alpha-phenethylamine (76.34 g, 0.63 m from Norse Chemical Co.). The mixture was briefly agitated and was allowed to stand at room temperature for 24 hours, giving a crystalline precipitate. After refrigeration for 3 days at 4° C., the mixture was filtered, and the solid was washed with 1.5 L ethyl acetate. The solid was dried at 40° C. for 6 hours under vacuum to constant weight, yielding 154.9 g, 0.39 mol., 62.0% recovery of a white solid, mp 149°–151° C.

| Rotation $[\alpha]_D^{23} = 28.2°$ (C = 1.06% methanol) | | |
| --- | --- | --- |
| Elemental analysis | | |
| TH | C 63.61 | H 9.15 | N 7.06 |
| F | C 63.41 | H 8.77 | N 6.92 |

In order to determine the isomer ratio, a small sample of the salt was regenerated to the acid by appropriately scaling down the procedure described on page 10 under "REGENERATION OF 4TH RECRYSTALLIZATION". HPLC of this product yields the isomer ratio.

| mp 101–104° C. | S Isomer | R Isomer |
| --- | --- | --- |
| | 74.97% | 25.03% |
| Rotation $[\alpha]_D^{23} = -36.4°$ (C = 1.02% in methanol). | | |

2nd Crystallization

The salt product from the 1st crystallization (153.5 g, 0.387 moles) is dissolved in 12.62 L of 98.6% ethyl acetate 1.3% methanol at 65° C. This is allowed to cool to room temperature with occasional agitation over five hours, giving a fibrous, solid precipitate. The mixture is refrigerated overnight at 3° C. The solid is filtered, washed with 1 L ethyl acetate and is dried to constant weight in vacuo at 40° C., giving a white solid, 123.5 g, 0.31 moles, 80.4% recovery mp 150°–3° C.

| Rotation $[\alpha]_D^{23}$ = −29.8° (C = 0.97% in methanol.) | | |
|---|---|---|
| Elemental Analysis: | | |
| TH  L 63.61 | H 9.15 | N 7.06 |
| F  L 63.57 | H 9.18 | N 7.00 |

The isomer ratio of the product of the second crystallization is determined by regeneration of the acid from the salt as mentioned before, giving a white solid. mp 112°–116° C.

| Rotation $[\alpha]_D^{23}$ = −38.6° (C = 1.02% in methanol) | | |
|---|---|---|
| Elemental Analysis | | |
| TH  C 56.71 | H 9.15 | N 5.09 |
| F  C 56.69 | H 9.02 | N 4.95 |

Isomer ratio following 2nd crystallization
3R: 7.91%; 3S: 89.54%; By HPLC
3rd Crystallization The salt product from the 2nd crystallization (122.2 g, 0.31 mole) is dissolved on 6 L hot ethyl acetate 99%/methanol 1%. The mixture is cooled to room temperature over 4 hours with occasional agitation, followed by refrigeration at 3° C. overnight. A solid precipitates, which is filtered, washed with 1 L ETOAC and dried to constant weight in vacuo at 40° C. giving a white solid, 107.8 g, 0.2 moles, 88% recovery. mp 151°–153° C.

| Rotation $[\alpha]_D^{23}$ −31.1° (C = 0.95% in methanol) | | |
|---|---|---|
| Elemental Analysis: | | |
| TH  C 63.61 | H 9.15 | N 7.06 |
| F  C 63.42 | H 8.98 | N 6.93 |

The isomer ratio of the product of the third crystallization is determined by regeneration of the acid from the salt as mentioned before, giving a white solid, mp 114°–118° C.

| Rotation $[\alpha]_D^{23}$ = −40.2° (C = 1.02% in methanol) | | |
|---|---|---|
| Elemental Analysis | | |
| TH  C 56.71 | H 9.15 | N 5.09 |
| F  C 56.47 | H 9.01 | N 4.94 |

Isomer ratio of 3rd crystallization
3R: 3.72%; 3S: 93.61%; by HPLC
4th Crystallization The salt product from the 3rd crystallization 105.9 g, 0.27 moles) is dissolved in 4.5 L hot ethyl acetate 99.5%/methanol 0.5%. The mixture is cooled to room temperature over 2 hours, followed by refrigeration at 3° C. overnight. A solid is filtered off, washed with 1.0 L ethyl acetate, and dried to constant weight in vacuo at 40° C., giving a white solid, 97.8 g, 0.246 moles, 90.7% recovery, mp 153°–4° C.

| Rotation $[\alpha]_D^{23}$ = −30.3° (C = 1.15% in methanol) | | |
|---|---|---|
| Elemental Analysis | | |
| TH  C 63.61 | H 9.15 | N 7.06 |
| F  C 63.49 | H 9.05 | N 6.94 |

The isomer ratio of the product of the fourth crystallization is determined by regeneration of the acid from the salt as mentioned before giving a white solid, mp 118°–120° C.

| Rotation $[\alpha]_D^{23}$ = −39.7° (C = 1.01% in methanol) | | |
|---|---|---|
| Elemental Analysis: | | |
| TH  C 56.71 | H 9.15 | N 5.09 |
| F  C 56.69 | H 8.81 | N 5.05 |

Isomer ratio of 4th crystallization
3R: 2.63%; 3S: 93.37%; By HPLC.
Regeneration of 4th Crystallization The salt product of the 4th crystallization (95.5 g, 0.24 moles) is suspended on 3 L ethyl acetate at 0° C. The mixture is extracted twice with 500 ml 1N hydrochloric acid at 0° C. and twice with 500 ml saturated sodium chloride solution. The organic phase is dried over magnesium sulfate, filtered, and the solvent removed in vacuo, giving an oil. The oil is dissolved in 500 ml diethyl ether, to which is charged 2 L Hexane, giving a precipitate. The mixture is heated to reflux.

The resultant solution is then gradually cooled to room temperature, followed by removal of diethyl ether in vacuo. The mixture is refrigerated at 3° C. overnight, giving a precipitate. The solid is filtered, washed with 1 L hexane, and dried to constant weight in vacuo at 40° C., giving a white solid, 58.1 g, 0.21 moles, 87.6% recovery. Mp 118°–120° C. 71.7% overall yield of the available 3S, 4S isomer.

| Rotation $[\alpha]_D^{23}$ = −39.6° (C = 0.98% in methanol.) | | |
|---|---|---|
| Elemental Analysis | | |
| TH  C 56.71 | H 9.15 | N 5.09 |
| F  C 56.93 | H 8.89 | N 5.00 |

Isomer Ratio
3S: 100.00% by HPLC

Rich, et al., in *J. Org. Chem.*, 43, 3624 (1978) reported 3S, 4S Boc statine Mp 117°–118° C., $[\alpha]_D^{23} = -39.5°$ (C=0.12% in CH$_3$OH)

For synthetic purposes, it may be desirable to leave the Boc protecting group intact; however the product can be converted to statine by removing the protecting group via conventional techniques. Removal via acidification, eg., with dilute trifluoroacetic acid or other suitable reagent is preferred.

While the invention is described above as employing four crystallization steps, it is contemplated that a lesser or greater number of such steps be used.

Other conventional recovery techniques may be used in combination with or, in place of, one or more of the steps described above.

Reasonable variations, such as those which would occur to a skilled artisan, can be made herein without departing from the scope of the invention.

I claim:

1. A process for producing 3S, 4S-Boc-Statine which comprises the steps of:
   (1) forming the R-(+)-alpha-phenethylamine salts of a mixture of 3RS, 4S isomers in a solvent,
   (2) fractionally crystallizing the 3S, 4S salt from the mixture, and
   (3) regenerating the free 3S, 4S-Boc-Statine.

* * * * *